Feb. 9, 1937. C. C. HENRY Plant Pat. 234

AVOCADO

Filed Nov. 26, 1935

INVENTOR.
Charles C Henry

BY A. B. Bowman
ATTORNEY.

Patented Feb. 9, 1937 Plant Pat. 234

UNITED STATES PATENT OFFICE

234

AVOCADO

Charles C. Henry, Escondido, Calif., assignor of one-half to Jesse L. Jones, Escondido, Calif.

Application November 26, 1935, Serial No. 51,606

1 Claim. (Cl. 47—62)

My discovery relates to a new and improved sport of the avocado fruit which has certain characteristics which are highly desirable as follows:

First, a novel fruit of the avocado.

Second, a fruit of the avocado in which the seed is extremely small in proportion to the size of the fruit.

Third, a fruit of the avocado in which the seed is loose in its cavity when the fruit is mature.

Fourth, a fruit of the avocado in which the texture of the fruit is very smooth and free from fiber.

Fifth, a fruit of the avocado in which the fruit is delicious, rich, and of nutty flavor and has a very high oil content.

Sixth, a fruit of the avocado which matures quickly and whose tree is a heavy producer.

Seventh, a fruit of the avocado which does not readily decay after maturity and whose flavor remains the same for a considerable time after maturity, and the flesh retains its color for several months after maturity.

Figure 1:
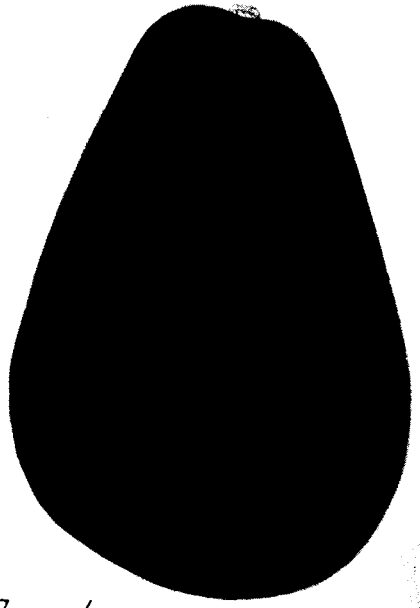
Figure 2:
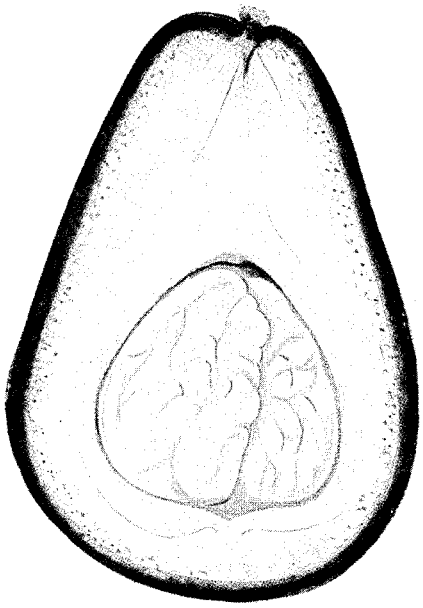
Figure 3:
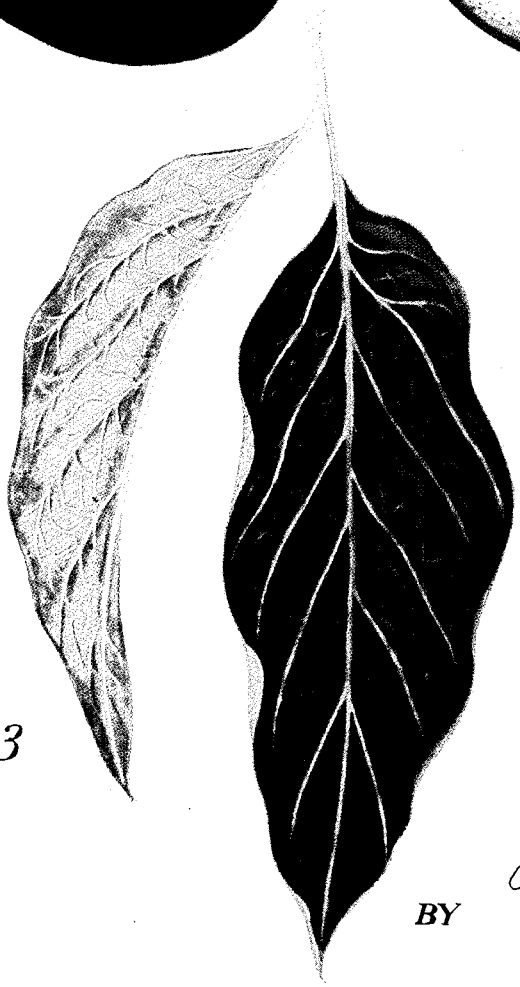

With these and other characteristics in view as will appear hereinafter, my invention consists of a certain novel fruit of the avocado as will be hereinafter described in detail and particularly set forth in the appended claim, reference being had to the accompanying drawing in which:

Figure 1 is a side elevational view in color of the fruit when ripe. Fig. 2 is a longitudinal section of the fruit in color when ripe, and Fig. 3 is a perspective view in color of two leaves with their petioles of a tree that produces the fruit and illustrating the foliage thereon. The original tree was a sport derived from the Mexican seedling and was simply discovered as a tree in the fall of 1931 near Escondido, California, and reproduced by budding or grafting by applicant. This tree was not propagated previous to its discovery by applicant.

The principal detailed distinguishing characteristics of my new fruit of the avocado are particularly apparent in that it is broadly obovate, of medium size, weighing 12 to 14 ounces, smooth, glossy, and deep maroon purple exterior with bronze colored speckles, and the seed extremely small in proportion to the size of the fruit and loose in the cavity when the fruit is mature. It has a rich, nutty flavor and high oil content, being 18 per cent.

*Technical description of fruit*

The fruit weighs from 12 to 14 ounces when mature, broadly obovate in shape, surface smooth, glossy, deep maroon purple with bronze speckles when fully mature, rind very thin, pulp is smooth and free from fiber, average oil content 18 per cent and yellow in color with definite green strip near the surface, seed relatively small and loose when the fruit is mature.

*Technical description of tree*

The tree is a fast upright grower and blossoms in March and April. The fruit matures in from 7 to 9 months from the time of blossom, the maturity season being from September to November and the tree bears the next year after budding. The foliage is long, dark green leaf about eight inches long when full grown and has a wavy edge. The budded tree shows all characteristics of the sport. The fruit is distributed throughout the inside and outside of the tree, the outer fruit being exposed.

Having thus described my invention, what I claim as new and desire to secure by Letters Patent is:

The avocado variety herein disclosed, characterized by fruit which when ripe has exterior shape broadly obovate, surface smooth and glossy, color of deep maroon purple with bronze speckles, interior color yellow with definite green strip near the surface, flesh smooth, free from fiber and with rich nutty flavor, with high oil content, seed relatively small and loose when matured.

CHARLES C. HENRY.